(12) United States Patent
Becker et al.

(10) Patent No.: US 6,712,757 B2
(45) Date of Patent: Mar. 30, 2004

(54) ENDOSCOPE SLEEVE AND IRRIGATION DEVICE

(75) Inventors: Stephen Becker, 680 N. Lake Shore Dr. #1525, Chicago, IL (US) 60611; Eleanor Laser, Lincolnwood, IL (US); William Barnhart, Iowa City, IA (US)

(73) Assignee: Stephen Becker, Chicago, IL (US)

( * ) Notice: Subject to any disclaimer, the term of this patent is extended or adjusted under 35 U.S.C. 154(b) by 0 days.

(21) Appl. No.: 09/858,785

(22) Filed: May 16, 2001

(65) Prior Publication Data

US 2002/0173699 A1 Nov. 21, 2002

(51) Int. Cl.[7] .............................................. A61B 1/015
(52) U.S. Cl. ........................ 600/121; 600/114; 600/157; 600/158
(58) Field of Search ................................ 600/114, 138, 600/153, 156, 157, 158, 159, 121, 122, 123

(56) References Cited

U.S. PATENT DOCUMENTS

| | | | |
|---|---|---|---|
| 3,903,877 A | | 9/1975 | Terada |
| 3,980,078 A | | 9/1976 | Tominaga |
| 4,836,187 A | | 6/1989 | Iwakoshi |
| 4,860,731 A | | 8/1989 | Matsuura |
| 4,991,564 A | * | 2/1991 | Takahashi et al. .......... 600/123 |
| 4,991,565 A | * | 2/1991 | Takahashi et al. .......... 600/123 |
| 5,191,878 A | | 3/1993 | Iida |
| 5,207,213 A | | 5/1993 | Auhll |
| 5,312,399 A | * | 5/1994 | Hakky et al. .................. 606/15 |
| 5,386,817 A | * | 2/1995 | Jones .......................... 138/108 |
| 5,464,008 A | | 11/1995 | Kim |
| 5,549,541 A | * | 8/1996 | Muller ........................ 600/105 |
| 5,575,756 A | | 11/1996 | Karasawa |
| 5,637,075 A | | 6/1997 | Kikawada |
| 5,718,709 A | * | 2/1998 | Considine et al. .......... 606/115 |
| 5,807,240 A | * | 9/1998 | Muller et al. ............... 600/135 |
| 5,810,770 A | * | 9/1998 | Chin et al. .................... 604/65 |
| 5,855,549 A | * | 1/1999 | Newman ..................... 600/135 |
| 5,989,183 A | * | 11/1999 | Reisdorf et al. ............ 600/121 |
| 6,282,442 B1 | * | 8/2001 | DeStefano et al. ........... 604/21 |
| 6,354,992 B1 | * | 3/2002 | Kato .......................... 600/157 |
| 6,409,657 B1 | * | 6/2002 | Kawano ..................... 600/157 |
| 6,428,510 B1 | * | 8/2002 | Kadan .................... 604/164.04 |

OTHER PUBLICATIONS

ClearESS™ advertisement tearsheet.

* cited by examiner

*Primary Examiner*—John P. Leubecker
(74) *Attorney, Agent, or Firm*—Michael Best & Friedrich LLP

(57) ABSTRACT

A sleeve for holding an endoscope used in surgical procedures including a hollow cylinder for receiving the endoscope, a docking member at the proximal end of the cylinder for receiving the viewing hub of the endoscope, a continuous suction supply adjacent the distal end of the cylinder, and a pressurized fluid supply for use when needed to clean the window of the endoscope.

19 Claims, 2 Drawing Sheets

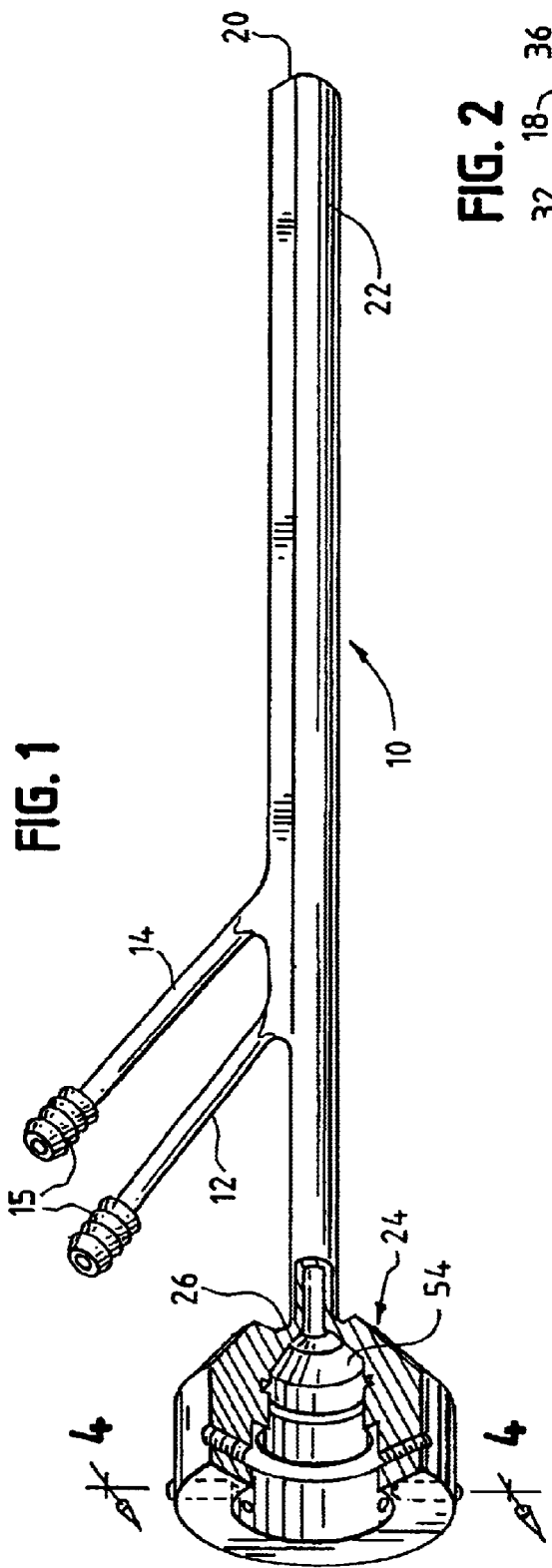
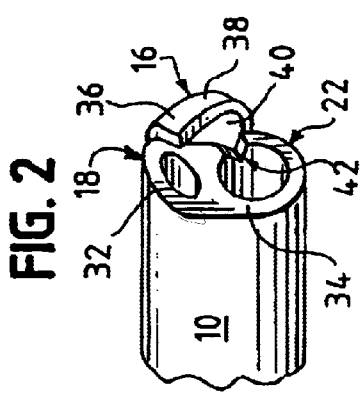
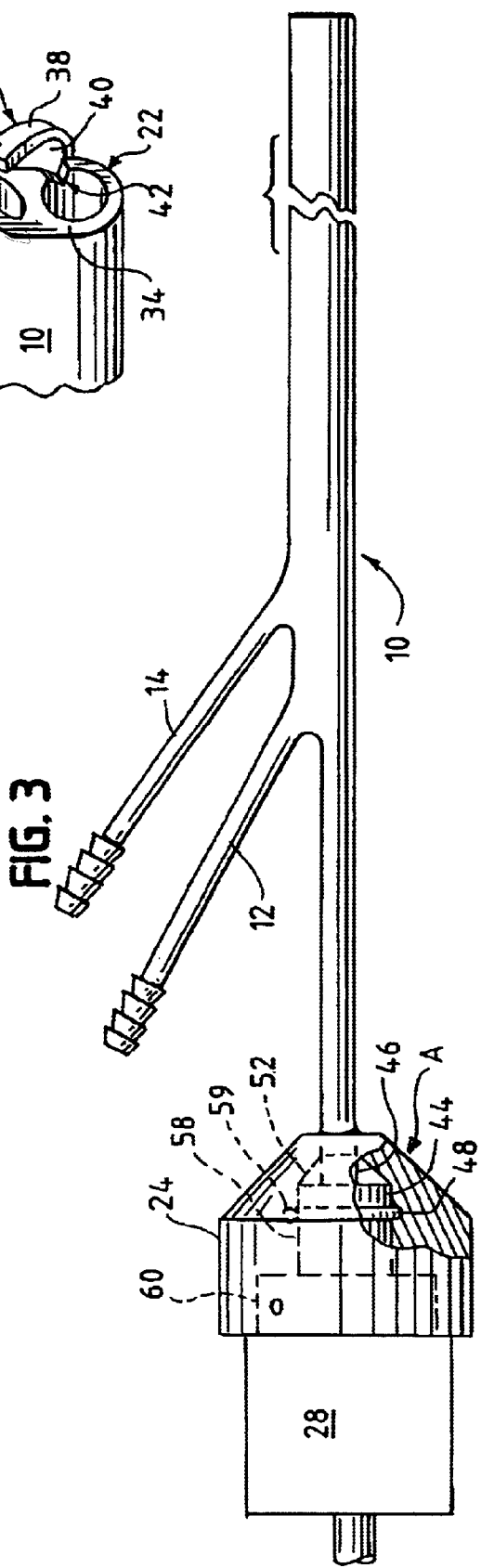

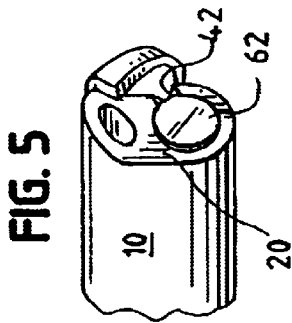
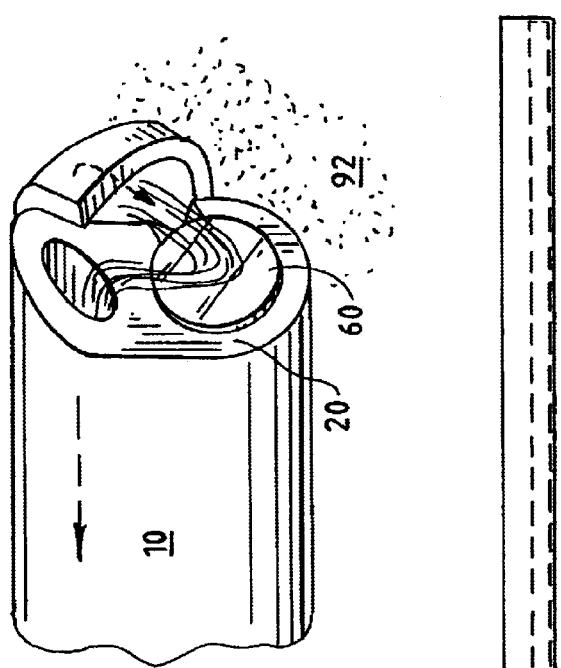
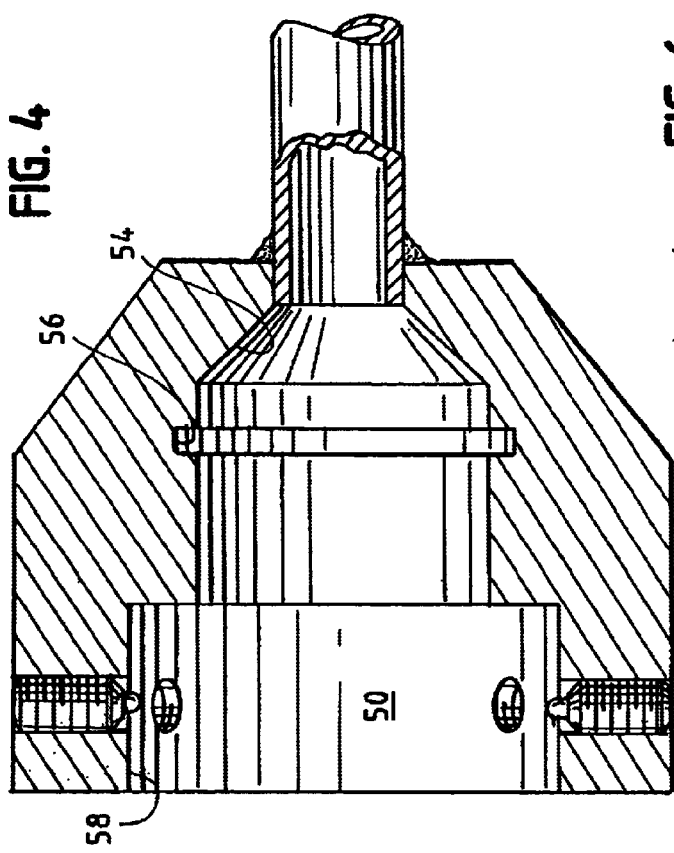
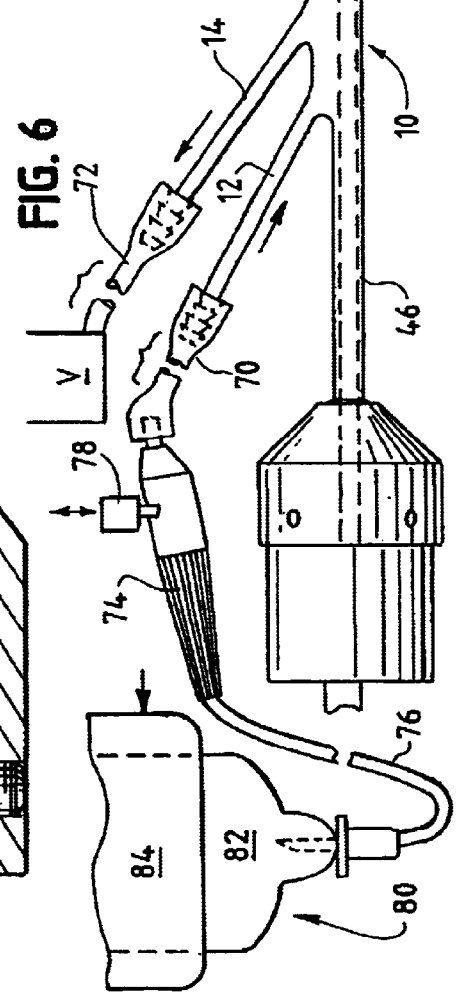

ENDOSCOPE SLEEVE AND IRRIGATION DEVICE

BACKGROUND OF THE INVENTION

This invention relates to an endoscope sleeve and, more particularly, to a sleeve for endoscopes used in surgical procedures which provides continuous suction and selective application of fluid to clean the endoscope window and also to clean or irrigate the operative field with a fine fluid spray.

Generally, endoscopes designed for surgery are adapted to be inserted in a body cavity, such as the nasal cavity, the pituitary cavity, the cranial cavity, or the middle ear. Surgical endoscopes are used to observe the condition of a body part within the cavity through a window at the distal end of the endoscope while surgical procedures are performed on that body part using instruments with elongated shafts and cutting tips inserted alongside the endoscope. Surgical endoscopes intended to be used with the sleeve of the present invention, like the 4 mm. sinus endoscopes available from Karl Storz and Smith & Nephew Richards, are to be distinguished from the much longer and thinner flexible endoscopes typically used only for examination and diagnostic purposes. Such surgical endoscopes should also be distinguished from laporoscopes used in laporoscopy where continuous pressure is typically required to keep the field inflated.

Currently, surgical endoscopes are provided with various devices for cleaning the surface of the distal window as it becomes soiled and fogged during the course of procedures conducted within the body cavity. These devices supply fluid and/or suction to the area of the distal window in various complex arrangements. The prior devices, however, are less than satisfactory in environments such as the nasal cavity, where the endoscope window is nearly continuously being soiled or fogged as surgical procedures are conducted. These prior art devices are often ineffective in quickly and effectively removing the fluids and tissue which accumulate on the endoscope window during the course of the surgical procedure. Such devices also typically do not supply continuous suction to the operative site, including when a window cleaning operation is underway, which is highly desirable.

It is essential to have a clear field in order to see the anatomy during the course of endoscopic surgical procedures. The nasal cavity, for example, is a particularly difficult environment because of the substantial mucus flow produced there and the requirement that a clear operative field be maintained. For example, when it is not possible to see through the endoscope, there is a danger that a continuously active suction port will touch surrounding nasal tissue, pulling it into the suction conduit, causing tissue damage and clogging the port.

Prior devices which do supply fluid for cleaning the endoscope window but do not carefully control the directionality of this fluid are problematic. These prior devices can project the fluid directly onto certain particularly sensitive surfaces within a cavity, such as a cranial cavity or an eye orbit damaging tissue in the cavity. Also, prior devices that do supply fluid for cleaning the endoscope window are often erratic in the amount of fluid delivered. This results in ineffective cleaning of the endoscope window.

Finally, many prior surgical endoscope sleeves are bulky and tend to impede the effective use of the surgical instruments used alongside the endoscope sleeve combination in the close quarters encountered, for example, in the nasal cavity, the pituitary cavity, the cranial cavity, or the middle ear. Such bulky surgical endoscope sleeves tend to prevent or impair proper alignment of instruments with the endoscope.

SUMMARY OF THE INVENTION

It is accordingly an object of this invention to provide an endoscope sleeve that can be easily adapted for use with different endoscopes for providing selective and effective cleaning and defogging of the endoscope window, and irrigation and suction to operative sites where the device is being used.

Another object of the present invention is to provide an endoscope sleeve that irrigates the operative field with a fluid spray.

Yet another object of the present invention is to provide an endoscope sleeve that provides continuous suction to clear away debris, smoke, etc. produced in the cavity during the course of surgical procedures.

It is a further object of this invention to provide an endoscope sleeve that does not interfere with the entry, manipulation or alignment of instruments used in operative procedures under guidance of the endoscope.

A still further object of the present invention is to provide an endoscope sleeve that is particularly useful in endoscopic sinus surgery and in endoscopic pituitary surgery.

These and other objects and advantages of the invention will become apparent from the description and claims which follow.

BRIEF DESCRIPTION OF THE DRAWINGS

FIG. 1 is a perspective view of an empty sleeve in accordance with the present invention, cut away at its proximal end to highlight the mechanism provided for locking an endoscope in the sleeve;

FIG. 2 is a partial end view, in perspective, of the empty sleeve of FIG. 1;

FIG. 3 is an elevation view of the sleeve of FIG. 1 in which an endoscope has been mounted and in which the sleeve is cut away at its proximal end to show the proximal end of the endoscope resting in the sleeve;

FIG. 4 is an enlarged cross-sectional view of the distal end of the sleeve of the present invention taken along lines 4—4 of FIG. 1;

FIG. 5 is an end view of and end view of a sleeve in accordance with the invention and corresponding to that of FIG. 2, showing the suction and fluid ports disposed adjacent the window of an endoscope mounted in the device;

FIG. 6 is an elevation view of a sleeve in accordance with the present invention in which the fluid and pressure supply are connected to the sleeve; and FIG. 7 is an enlarged view of a portion of the distal end of the sleeve and endoscope of FIG. 6 demonstrating the manner in which an endoscope window is cleaned in accordance with the present invention.

DETAILED DESCRIPTION OF THE PREFERRED EMBODIMENTS

Turning first to FIGS. 1 and 2, a sleeve in accordance with the present invention is illustrated at 10. The sleeve includes a fluid inlet port 12 and a suction port 14, with both ports angled toward the proximal end of the sleeve. Each of the ports has a conventional nipple 15 for frictionally attaching hoses to supply fluid and suction as appropriate. Fluid inlet port 12 is in communication with a fluid conduit 16 which opens onto the distal end 20 of the sleeve while suction port 14 is in communication with a suction conduit 18 which also opens onto the distal end 20 of the sleeve. As explained in more detail below, the suction conduit transports fluid, mucus and smoke away from the operative field, and the fluid conduit supplies fluid (typically sterile saline) to the distal end of the sleeve to clean the distal window of an endoscope mounted in the sleeve.

The fluid and suction conduits are attached to the side of a hollow rigid cylinder 22 dimensioned to receive the outer tube of an endoscope. Cylinder 22 also includes an annular docking member 24 mounted to the proximal end 26 of cylinder 22.

As can be seen most clearly in the enlarged distal end view of the empty sleeve shown in FIG. 2, the distal end 32 of suction conduit 18 is a generally annular opening located in a plane which is generally perpendicular to the longitudinal axis of the sleeve. The distal end 34 of rigid cylinder 22 is similarly generally annular and lies generally in the same plane as the distal end of the suction conduit. This cylinder is preferably of a length just slightly shorter than the outer tube of the endoscope which is to be fitted to the sleeve so that the window at the distal end of the endoscope lies just beyond the distal end of the cylinder.

The distal end 36 of fluid conduit 16 is capped with an overhanging portion or hood 38 which is open on the side to provide a fluid outlet 40 opposite distal end 34 of cylinder 22. Additionally, a notch 42, preferably half moon in shape, may be cut out of the distal end of cylinder 22 to provide improved access to the endoscope window. As explained in more detail below, hood 38 insures that the fluid passing through fluid conduit 16 and out of outlet 40 will be directed against the distal window of the endoscope mounted in sleeve 10.

In FIG. 3, an endoscope 28 for use in endoscopic cavity surgery is shown mounted in cylinder 22 of sleeve 10 of the invention. Docking member 24 is cut away at A to show the viewing hub 44 at the proximal end of the elongated tube 46 of the endoscope mounted in docking member 24.

Docking member 24 is illustrated in more detail in FIG. 4. This member includes a cavity 50 configured to snugly receive the viewing hub of the endoscope with the conical leading surface 52 of the hub (FIG. 3) abutting a corresponding conical surface 54 in the docking member. An annular groove 56 is provided spaced from conical surface 54 to receive an "O" ring 59 which helps position the viewing hub in place in the sleeve and minimizes seepage through the sleeve. An enlarged cylindrical opening 58 is provided at the proximal end of the docking member to receive a corresponding enlarged proximal portion 60 (FIG. 3) of the viewing hub of the endoscope. Removal of the endoscope from the sleeve will require the application of sufficient force to displace the locking ring from the annular groove, whereupon the entire endoscope may be removed from the sleeve. Removal of the endoscope from the sleeve will require the application of sufficient force to pass "O" ring 56, whereupon the entire endoscope may be removed from the sleeve.

Thus, the scope is mounted in the sleeve by inserting tube 46 of the scope into cylinder 22 of the device until the viewing hub of the endoscope is fully seated in the docking member of the device. Turning now to FIG. 5, the window 62, at the distal end of endoscope tube 46 will now preferably be offset about 2 mm. to 3 mm. beyond the end of cylinder 22. Although the window of the endoscope will typically be perpendicular to the longitudinal axis of the endoscope, it may have angulations of up to 30°. Since the window extends such a short distance beyond from the end of cylinder 22, fluid directed from outlet 40 will perform the intended function at all of these angulations.

Turning now to FIG. 6, the endoscope sleeve of the present invention is shown with flexible air and suction hoses, 70 and 72 respectively, in place on nipples 15 of fluid and suction ports 12 and 14, connecting the suction and fluid ports to an appropriate supply of suction, and a high pressure supply of fluid. Preferably suction will be that conventionally supplied by the high continuous wall suction source available in the operating room.

Flexible hose 70 extending from the nipple on fluid port 12 is connected to a control valve 74, and a further portion of flexible tubing 76 which, in turn is connected to the high-pressure fluid source 80 as discussed below. This valve is a conventional on/off fluid control valve which is "off" until spring biased button 78 is pressed to turn "on" the fluid flow and returns to the "off" condition when the button is released. This valve is preferably located in the fluid line a substantial distance from the point of attachment of hose 70 to fluid port 12. It is preferred that this spacing be at least about 15 cm. Locating switch 74 off of the sleeve and away from the surgical field makes it possible to provide a particularly compact sleeve 10 which produces minimal obstruction of cutting and other instruments (not shown) inserted alongside the sleeve during the course of an endoscopic procedure. Additionally, this remote fluid on-off control can be handled, for example, by the surgeon's first assistant, surgical scrub nurse or other assistant who can act on either the surgeon's instructions or by watching the procedure proceeding on a monitor connected to the endoscope operating in a conventional manner.

The pressure provided at fluid source 80 should be at least about 100 cm to 120 cm of $H_2O$. One desirable way of providing this pressure is with a conventional bag of intravenous fluid 82 held in a pressure cuff 84 as is typically used to provide rapid intravenous administration. A conventional infusion pressure pump cannot supply sufficient fluid pressure. The application of this high pressure fluid is possible because the cavity in which the endoscopic procedure is performed communicates with the atmosphere, permitting the release of pressure introduced by the high-pressure fluid.

FIG. 7 shows high pressure fluid 90 (saline) directed against the surface of endoscope window 60 to defog and clean debris from the window and to produce a fine spray 92 as the fluid is deflected back from the window surface. The fluid must be provided at a pressure which greatly exceeds the suction force. Preferably, the fluid will be provided at a pressure of at least about 12 cm to 25 cm of $H_2O$ at the distal end of the fluid conduit. For example, a pressure of 150 mm of mercury may be provided on cuff 84 to produce fluid pressure sufficient to support a 40 cm column of water. This high pressure quickly and effectively cleans the surface of the endoscope window, irrigating the field and cleaning the end of the scope in a single operation. Thus, as the procedure proceeds, the surgeon will operate valve 74 from time to time to both clear the window of the endoscope and clear the entire operative area.

There has been described herein an endoscope sleeve free from the shortcomings of the prior art. It will be apparent to those skilled in the art that modifications may be made without departing from the spirit and scope of the invention. Accordingly, it is not intended that the invention be limited except as may be necessary in view of the appended claims.

What we claim is:

1. A sleeve for holding an endoscope used in surgical procedures performed in a body cavity, the endoscope having a viewing hub at its proximal end and a window at its distal end, comprising:
   a hollow cylinder for receiving the outer tube of the endoscope, the endoscope having a viewing hub at its proximal end and a window at its distal end;
   a docking member at the proximal end of the cylinder to receive and removably retain the viewing hub of the endoscope, with its distal window adjacent the distal end of the cylinder;
   means for continuously directing suction to an inlet in the suction means adjacent the distal end of the cylinder; and
   means for directing pressurized fluid when desired from an outlet in the pressurized fluid means adjacent the distal end of the cylinder against the endoscope window to clear the window and to produce a fluid spray projecting away from the window for irrigating the body cavity.

2. The sleeve of claim 1 in which the hollow cylinder is of a length which insures that the endoscope window will be positioned about 2 mm to 3 mm beyond the end of the cylinder.

3. The sleeve of claim 1 in which the pressurized fluid is supplied through a fluid line comprising flexible tubing connected to a high-pressure fluid source.

4. The sleeve of claim 3 in which a control valve is positioned in the fluid line to control the flow of fluid to the sleeve.

5. The sleeve of claim 4 in which the valve is biased in the "off" position, permitting fluid to flow through the tubing only while the valve is held in the "on" position.

6. The sleeve of claim 4 in which the valve is located in the fluid line at a spacing of at least about 15 cm from the endoscope sleeve.

7. The sleeve of claim 3 in which the pressure provided at the fluid source is at least about 100 cm to 120 cm of $H_2O$.

8. The sleeve of claim 3 in which the fluid source is an intravenous fluid bag held in a pressure cuff.

9. The sleeve of claim 8 in which a pressure of 150 mm of mercury is provided to the cuff to produce fluid pressure in the cuff sufficient to support a 40 cm column of water.

10. The sleeve of claim 1 in which the fluid is supplied at the outlet adjacent the distal end of the cylinder at a pressure of at least about 12 cm to 25 cm of $H_2O$.

11. The sleeve of claim 1 in which the outlet in the pressurized fluid means includes a hood for directing the fluid against the endoscope window.

12. A sleeve for holding an endoscope used in surgical procedures, the endoscope having a viewing hub at its proximal end and a window at its distal end, comprising:
   a hollow cylinder for receiving the outer tube of an endoscope, the endoscope having a viewing hub at its proximal end and a window at its distal end, the window being positioned about 2 mm to 3 mm beyond the end of the hollow cylinder;
   a docking member at the proximal end of the cylinder to receive and removably retain the viewing hub of the endoscope with its distal window adjacent the end of the cylinder;
   means for continuously supplying suction to an inlet adjacent the distal end of the cylinder; and
   means for supplying pressurized fluid when desired to an outlet adjacent the distal end of the cylinder in which the pressurized fluid is supplied through a fluid line comprising flexible tubing connected to a high-pressure fluid source, a control valve is positioned in the fluid line to control the flow of fluid to the sleeve, and the valve is located in the fluid line at a spacing of at least about 15 cm from the endoscope sleeve.

13. The system of claim 12 in which the hollow cylinder is of a length which insures that the endoscope window will be positioned about 2 mm to 3 mm beyond the end of the cylinder.

14. The sleeve of claim 12 in which the valve is biased in the "off" position, permitting fluid to flow through the tubing only while the valve is held in the "on" position.

15. A method for performing a desired endoscopic surgery in a body cavity comprising:
   providing a surgical endoscope with a viewing hub at its proximal end, a window at its distal end and a sleeve for holding the endoscope, the sleeve including a hollow cylinder for receiving the endoscope, an unobstructed suction conduit for continuously directing suction to an inlet adjacent the distal end of the cylinder, and means for directing pressurized fluid when desired to an outlet, adjacent the distal end of the cylinder;
   positioning the distal end of the hollow cylinder within a body cavity;
   positioning surgical instruments alongside the endoscope, as needed;
   performing the desired endoscopic surgery in the cavity using the surgical instruments while continuously supplying suction through the suction conduit to the inlet in the conduit adjacent to the distal end of the cylinder, and supplying pressurized fluid to the outlet adjacent to the distal end of the cylinder to direct the fluid against the endoscope window as needed to clear debris and fogging from the window of the endoscope, and to produce a fine spray projecting away from the window to irrigate the body cavity.

16. The method of claim 15 in which the pressurized fluid is supplied at the outlet adjacent the distal end of the cylinder at a pressure of at least about 12 cm to 25 cm of $H_2O$.

17. The method of claim 15 in which the fluid source is an intravenous fluid bag held in a pressure cuff, and a pressure of 150 mm of mercury is provided to the cuff to produce fluid pressure in the cuff sufficient to support a 40 cm column of water.

18. The method of claim 17 in which the pressure provided at the cuff is at least about 100 cm to 120 cm of $H_2O$.

19. The method of claim 15 in which the endoscope window is positioned about 2 mm to 3 mm beyond the end of the cylinder.

* * * * *